United States Patent

Morito et al.

[11] Patent Number: 6,118,476
[45] Date of Patent: Sep. 12, 2000

[54] CCD MICROSCOPE

[75] Inventors: Yuhkoh Morito, Yokohama; Junichi Arai, Kamisato-machi; Kouichi Watanabe, Yono, all of Japan

[73] Assignee: Moritex Corporation, Tokyo, Japan

[21] Appl. No.: 09/113,505

[22] Filed: Jul. 10, 1998

[30] Foreign Application Priority Data

Apr. 21, 1998 [JP] Japan .................................. 10-110652

[51] Int. Cl.⁷ ...................................................... H04N 7/18
[52] U.S. Cl. .................................................. 348/65; 348/80
[58] Field of Search .................................. 348/61, 65, 68, 348/77, 79, 80

[56] References Cited

U.S. PATENT DOCUMENTS 5,691,840  11/1997  Bae .......................................... 359/386

FOREIGN PATENT DOCUMENTS 2-207401  8/1990  Japan .
3-135276  6/1991  Japan .
4-214523  8/1992  Japan .

Primary Examiner—Bryan Tung
Attorney, Agent, or Firm—Greenblum & Bernstein, P.L.C.

[57] ABSTRACT

A CCD microscope includes: two polarized light illumination systems for irradiating polarized lights having vibrating directions in perpendicular to each other selectively to an object to be observed, and an analyser disposed on an optical path from the object to a CCD device for picking-up an image of the object, the analyser having a vibrating direction in parallel with the vibrating direction of the polarized light from one polarized light illumination system, and in perpendicular to the vibrating direction of the polarized light from the other polarized light illumination system. The surface state of the object is picked-up by a polarized light of one polarized light illumination system that is kept unchanged for the polarized state upon reflection on the surface, while the inner state of the object is picked-up by a polarized light of the other polarized light illumination system that is changed for the polarized state.

2 Claims, 1 Drawing Sheet

CCD MICROSCOPE

BACKGROUND OF THE INVENTION

1. Field of the Invention

This invention concerns a CCD (Charge-Coupled Device) microscope for observing an object such as skins or scalps by projecting them at a predetermined magnifying ratio on a screen.

2. Related Art Statement

A CCD microscope for observing skins and like other objects under magnification comprises a CCD device, a lens system for focusing a magnified image of an object on an imaging surface of the CCD device and an illumination device for irradiating an illumination light to the object.

The surface state of skin such as skin roughening and texture can be observed by focusing a light reflected from the skin surface, and the inner state of the skin such as spot and dullness can be observed by focusing a light scattered in the inside of the skins while cutting off the light reflected on the surface.

Therefore, the CCD microscope of the prior art comprises two illumination systems, namely, a non-polarized light illumination system and a polarized light illumination system as an illumination device, and a polarizing filter is intervened in an optical path from an object to the CCD device. This filter functions as an analyser having a polarizing direction in perpendicular to the polarized illumination light of the polarized light illumination system (refer to Japanese Patent Laid-Open Hei 4-214523).

The polarized light illumination system comprises a light source for illumination of a polarized light and a polarizing filter as a polarizer for linearly polarizing the light irradiated from the light source. In the illumination light linearly polarized by the polarized light illumination system, a light reflected on the skin surface as an object and kept unchanged for the polarized state is cut off by the analyser before incidence to the CCD device and only the light scattered in the inside of the skin and changed for the polarizing direction enters the CCD device. Accordingly, spot and dullness in the inside of the skin can be observed by the illumination from the polarized light illumination system.

Further, since the illumination light irradiated from the non-polarized light illumination system is a natural light and includes all sorts of polarizing directions even after reflection at the skin surface, it enters the CCD device even if a portion thereof is cut off by the analyser. Therefore, the skin surface can be observed by the irradiation of the non-polarized light illumination system.

However, when the object is illuminated by the non-polarized light illumination system, the light after random reflection in the inside of the skin also includes all sorts of polarizing directions and, accordingly, enters the CCD device even if a portion thereof is cut off by the analyser, so that both of the surface state and the inner state of the skin, when picked-up, are displayed simultaneously to bring about a difficulty in the observation.

Further, comparing images obtained by illumination from the polarized light illumination system and those from the non-polarized light illumination system, since the illumination light from the polarized light illumination system is transmitted through the polarizer, it is dark as compared with the illumination light from the non-polarized light illumination system. Therefore, images obtained by illumination from the non-polarized light illumination system becomes entirely darkened, to thereby possibly cause an erroneous judgment of taking an area without spot and dullness for actual spot and dullness.

Therefore, the brightness of the illumination light of the polarized light illumination system was increased or that of the non-polarized light illumination system was decreased for adjusting the optical intensity of them, but entire images illuminated from the polarized light illumination system still appeared somewhat darker.

As a result of a further study made by the present inventor for making the cause clearer, it was found that the darkness of the images when illuminated from the polarized light illumination system is caused not only by the optical intensity but also by the difference of the color of the illumination light.

Then, when a color filter for adjustment of color temperature was used in the non-polarized light illumination system, and when comparing the images on the screen of both of the cases, tones of the entire screens were identical, so that erroneous judgment of taking an area without spot and dullness for actual spot and dullness could be avoided.

However, color adjustment by interposing the color filter was troublesome and, if the skin was illuminated by the non-polarized light illumination system and since, both of the surface state and the inner state of the skin were projected simultaneously even after color adjustment, the problem of the difficulty for the observation of the surface state was still left undissolved.

OBJECT OF THE INVENTION

It is, accordingly, a technical object of the present invention, in a case of observing the surface state and the inner state of an object to be observed by irradiating two kinds of illumination lights selectively on the object, to eliminate the difference of tones of the images caused by the difference of the color between the illumination lights and enable to pick-up images while clearly distinguishing the light reflected on the surface of the object from the light scattered in the inside of the object.

SUMMARY OF THE INVENTION

The foregoing object can be attained in accordance with the present invention by a CCD microscope comprising two polarized light illumination systems for irradiating polarized lights having vibrating directions in perpendicular to each other selectively to an object to be observed, and an analyser disposed on an optical path X from the object to a CCD device for picking-up an image of the object, the analyser having a vibrating direction in parallel with the vibrating direction of a polarized light from one polarized light illumination system, and in perpendicular to the vibrating direction of a polarized light from the other polarized light illumination system.

According to the present invention, when the polarized light having a vibrating direction in parallel with the vibrating direction of the analyser (that is, so-called parallel nicols) is irradiated from one of the polarized light illumination systems, a light reflected at random in the inside of the object is cut off by the analyser since the polarized state is changed, whereas a light reflected on the surface of the object and kept unchanged for the polarized state transmits the analyser and reaches the CCD device.

Accordingly, the inner state of the object such as spot and dullness is not picked up but only the surface state of the object such as skin roughening or texture is projected with emphasis.

Further, when a polarized light having a vibrating direction in perpendicular to the vibrating direction of the analyser (that is, so-called cross nicols) is irradiated as an illumination light from the other of the polarized light illumination systems, a light reflected on the surface of the object and kept unchanged in the identical polarized state is cut off by the analyser and only the light reflected at random and changed for the polarized state in the inside of the object reaches the CCD device.

Accordingly, the surface state of the object such as the skin roughening or texture is not picked up but only the inner state of the object such as spot and dullness is projected.

For instance, when polarizing filters of an identical type are arranged in each of the polarized light illumination systems such that vibrating directions of them are in perpendicular to each other to obtain two kinds of polarized lights, optical properties of each of the polarized lights are quite equal with each other excepting for the vibrating direction, and there is no requirement for color adjustment by using an additional color filter or the like.

Therefore, when comparing images obtained by illumination of the object from each of the polarized light illumination systems, erroneous judgment caused by the difference of the brightness or the tone of the images can be avoided.

BRIEF DESCRIPTION OF THE ACCOMPANYING DRAWINGS

The present invention will be explained more specifically by way of a preferred embodiment with reference to the accompanying drawings, wherein FIG. 1 is a cross sectional view illustrating a main portion of a CCD microscope according to the present invention; and FIG. 2 is an exploded perspective view of the CCD microscope.

DESCRIPTION OF THE PREFERRED EMBODIMENT

Figure 1:
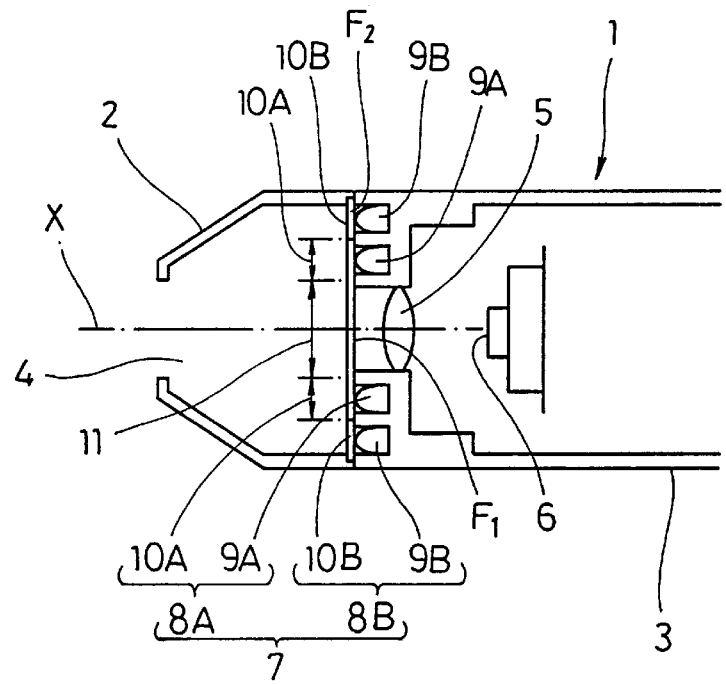
Figure 2:
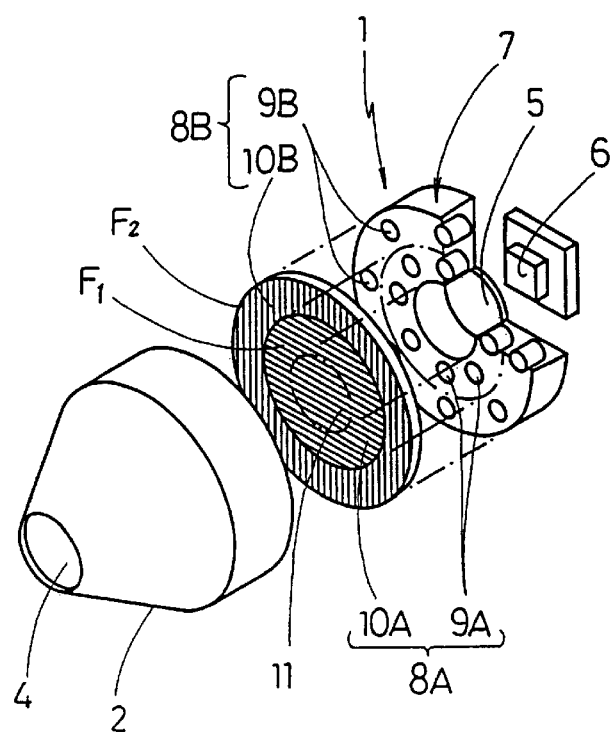

A CCD microscope 1 according to the present invention comprises a cylinder 3 having a head 2 formed at the top end to be in contact with an object, in which are disposed a lens 5 for enlarging an image taken from an observation hole 4 apertured in the head 2, a CCD device 6 for picking-up an image transmitting the lens 5 and an illumination device 7 for irradiating an illumination light to the observation hole 4 formed in the head 2.

The illumination device 7 has two polarized light illumination systems 8A and 8B for selectively irradiating polarized lights having vibrating directions in perpendicular to each other.

In each of the polarized illumination systems 8A and 8B, a plurality of high luminance white LEDs (Light Emission Diode) 9A—, 9B—are arranged as double rings, a switching circuit is provided (not illustrated) for enabling selective emission of each of an outer ring and an inner ring, and two polarizers 10A and 10B having vibrating directions perpendicular to each other are disposed on every group of the LEDs 9A—, 9B—in each of the rings being opposed to the light emission surface of each LED.

Further, an analyser 11 having a vibrating direction in parallel with the vibrating direction of the polarized light of one polarized light illumination system 8A and in perpendicular to the vibrating direction of the polarized light of the other polarized light illumination system 8B is disposed on an optical path X from the observation hole 4 to the CCD device 6.

The polarizer 10A of one polarized light illumination system 8A is formed with a circular polarizing filter $F_1$ that functions also as the analyser 11, whereas the polarizer 10B of the other polarized light illumination system 8B is formed with an annular polarizing filter $F_2$ coaxially surrounding the outside of the polarizing filter $F_1$. The polarizing filters $F_1$ and $F_2$ have optical properties equal or substantially equal with each other excepting for the vibrating direction.

With such a constitution, the vibrating direction of the polarized light transmitting the polarizer 10A of one polarized light illumination system 8A is in parallel with the vibrating direction of the analyser 11, whereas the vibrating direction of a polarized light transmitting the polarizer 10B of the other polarized light illumination system 8B is in perpendicular to the vibrating direction of the analyser 11.

Accordingly, in the light irradiated from one polarization optical system 8A to the object, only the light kept unchanged for the polarized state transmits the analyser 11 and is picked-up by the CCD device 6. On the other hand, in the light irradiated from the other polarized light illumination system 8B to the object, only the light changed for the polarized state transmits the optical director 11 and is picked by the CCD device 6.

The foregoing constitution is an example of the present invention and the operation thereof is to be explained.

For instance, when a skin is to be picked-up under magnification, the head 2 is brought into contact with the skin and an image taken through the observation hole 4 apertured in the top end of the head is picked-up by the CCD device 6.

In a case of observing a skin surface, for example, degree of the skin roughness or fineness of the texture, a light is illuminated from the polarized light illumination system 8A in which the LEDs 9A—are disposed at the inside.

A light irradiated from the LEDs 9A—of the polarized light illumination system 8A is linearly polarized by being passed through the polarizer 10A, and irradiated on a portion of the skin situated at the observation hole 4, and a reflection light is passed through the analyser 11 and picked-up by the CCD device.

Since the polarizer 10A and the analyser 11 are formed with one identical polarizing filter $F_1$ and the vibrating directions of the lights transmitting therethrough are in parallel with each other, only the light reflected on the surface of the skin and kept unchanged for the polarized state transmits the analyser 11, whereas a light reflected at random in the inside of the skin and changed for the polarized state is cut off by the analyser 11.

Accordingly, only the light reflected on the surface of the skin is picked-up by the CCD device 6, so that degree of the skin roughness and fineness of the texture can be observed. Even if the spot and dullness are seen in the skin, when viewed with naked eyes, since they are caused by deposition of pigments in the inside of the skin, they are scarcely picked-up by the CCD device 6 when illuminated by the polarized light illumination system 8A.

When the spot and dullness in the inside of the skin are to be observed, illumination is made from the polarized light illumination system 8B having the LEDs 9B—disposed to the outside.

The light irradiated from the LEDs 9B—of the polarized light illumination system 8B is linearly polarized by being passed through the polarizer 10B, irradiated to a portion of the skin situated at the observation hole, and the reflection light is passed through the polarizer 11 and picked-up by the CCD device 6.

In this case, since the vibrating directions of the lights transmitting the polarizer 10B and the analyser 11 are in perpendicular to each other, the light reflected on the surface of the skin and kept unchanged for the polarized state is cut off by the analyser 11, while only the light reflected at random in the inside of the skin and changed for the polarized state transmits the analyser 11 and reaches the CCD device 6.

Accordingly, only the light reflected at random in the inside of the skin is picked-up by the CCD device 6 and only the spot and dullness can be observed, without projecting the surface state of the skin.

Since the polarized lights of the polarized light illumination systems 8A and 8B are formed by transmission through the polarizers 10A and 10B having optical properties equal with each other excepting for the vibrating direction, both of the polarized lights are different only in the vibrating direction and are quite equal with each other for other optical properties than described above, for example, color and optical intensity.

Accordingly, when comparing images illuminated by each of the polarized light illumination systems 8A and 8B, there is no worry of erroneous judgment of taking an entirely darkened area with no spot and dullness for actual spot and dullness owing to the difference of the brightness and the tone of the images.

While explanation has been made to the polarized light illumination systems 8A and 8B in a case where the LEDs 9A—, 9B—are arranged in the form of double rings, but the present invention is not restricted only to such an arrangement but the number and the arrangement of the LEDs may be varied optionally.

Further, the light source for each of the polarized light illumination systems 8A and 8B is not restricted only to such light emitting devices as LEDs 9A—, 9B—, but a light source may be, for example, a halogeno lamp from which a light is introduced by way of optical fibers.

Further, while explanation has been made to a case in which the polarizer 10A and the analyser 11 are constituted with one identical circular polarizing filter $F_1$, it will be apparent that different polarizing filters may be used separately for them.

Furthermore, vibrating directions of the polarizer 10A, the polarizer 10B and the analyser 11 have been explained such that the directions of the polarizer 10B and the polarizer 10A are in perpendicular to each other, the directions of the polarizer 10A and the analyser 11 are in parallel with each other, and the polarizer 10B and the directions of the analyser 11 are in perpendicular to each other. However, within such a range as not departing the gist of the invention, it is not always necessary that the vibrating directions are kept strictly in perpendicular to each other but it may suffice that they are kept substantially in perpendicular to each other. In the same manner, it is not always necessary that the vibrating directions are kept strictly in parallel with each other but it may suffice that they are kept substantially in parallel with each other.

Accordingly, the terms "in perpendicular to" and "in parallel with" regarding the vibrating directions also include "substantially in perpendicular to" and "substantially in parallel with", respectively, throughout the specification and the claims of the present application.

As has been described above, according to the present invention, when the object is illuminated by one of the polarized lights, only the light reflected on the surface of the object and kept unchanged for the polarized state reaches the CCD device to project the surface state. On the other hand, when the object is illuminated by the other of the polarized lights, only the light reflected at random and changed for the polarized state in the inside of the object reaches the CCD device to project the inner state. Therefore, the present invention provides an excellent effect capable of projecting the surface state and the inner state of the object while clearly distinguishing them.

In addition, each of the illumination lights has optical properties equal with each other excepting for the vibrating direction of the polarized light, so that there is no requirement for color adjustment by using, for example, an additional color filter, and erroneous judgment owing to the difference of the brightness or the tone of the images is less caused when comparing images picked-up from the object by each of the illumination lights.

What is claimed is:

1. A CCD microscope comprising:

two polarized light illumination systems for irradiating polarized lights having vibrating directions in perpendicular to each other selectively to an object to be observed, and an analyser disposed on an optical path from the object to a CCD device for picking-up an image of the object, said analyser having a vibrating direction in parallel with the vibrating direction of the polarized light from one polarized light illumination system, and in perpendicular to the vibrating direction of the polarized light from the other polarized light illumination system.

2. A CCD microscope as defined in claim 1, wherein the two polarized light illumination system are provided with a plurality of light emitting devices arranged as double rings, respectively, and enabled to emit light selectively from each of an outer ring and an inner ring, and two polarizers having vibrating directions in perpendicular to each other are disposed, respectively, on every group of the light emitting devices in each of the rings, being opposed to the light emitting surface of each of them.

* * * * *

UNITED STATES PATENT AND TRADEMARK OFFICE
CERTIFICATE OF CORRECTION

PATENT NO. : 6,118,476
DATED : September 12, 2000
INVENTOR(S) : M. MORITO et al.

It is certified that error appears in the above-identified patent and that said Letters Patent is hereby corrected as shown below:

At column 6, line 45 (claim 2, line 2) of the printed patent, "system" should be ---systems---

Signed and Sealed this

First Day of May, 2001

Attest:

NICHOLAS P. GODICI

Attesting Officer        Acting Director of the United States Patent and Trademark Office